(12) United States Patent
Paulista et al.

(10) Patent No.: US 7,365,051 B2
(45) Date of Patent: *Apr. 29, 2008

(54) COMPOUNDS WITH IMPROVED CARTILAGE-INDUCING AND/OR BONE-INDUCING ACTIVITY

(75) Inventors: Michael Paulista, Leimen (DE); Jens Pohl, Hambruecken (DE); Joachim Pabst, Reinheim (DE); Helmut Heide, Kelkheim (DE)

(73) Assignee: Biopharm Gesellschaft zur Biotechnologischen Entwicklung von Pharmaka mbH, Heidelberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 11/080,494

(22) Filed: Mar. 16, 2005

(65) Prior Publication Data

US 2005/0169965 A1 Aug. 4, 2005

Related U.S. Application Data

(63) Continuation of application No. 09/297,092, filed as application No. PCT/EP97/06463 on Nov. 19, 1997, now abandoned.

(30) Foreign Application Priority Data

Nov. 19, 1996 (DE) .............................. 196 47 853

(51) Int. Cl.
- *A61K 38/00* (2006.01)
- *A61K 9/14* (2006.01)
- *C07K 1/00* (2006.01)
- *A61F 2/00* (2006.01)
- *A61F 3/00* (2006.01)

(52) U.S. Cl. ..................... 514/2; 514/12; 530/350; 424/422; 424/423; 424/484

(58) Field of Classification Search .................... None
See application file for complete search history.

(56) References Cited

U.S. PATENT DOCUMENTS

| | | | |
|---|---|---|---|
| 4,596,574 A | 6/1986 | Urist | |
| 4,681,763 A | 7/1987 | Nathanson et al. | |
| 5,866,155 A | 2/1999 | Laurencin et al. | |

FOREIGN PATENT DOCUMENTS

| | | |
|---|---|---|
| WO | WO 91/05802 | 2/1991 |
| WO | WO 95/04819 | 2/1995 |
| WO | WO 95/32008 A1 | 11/1995 |

OTHER PUBLICATIONS

Attisano et al., Science, 296:1646-1647, 2002.
Miyazono et al., J Cell Physiol, 187(3):265-76, 2001.
Rosenberg et al., Gene Therapist, Heal Thyself, Science 287:1751, 2000.
Verma, Gene Therapy: beyond 2000. Mol. Ther..1:493,2000.

*Primary Examiner*—Sumesh Kaushal
(74) *Attorney, Agent, or Firm*—Rothwell, Figg, Ernst & Manbeck, P.C.

(57) ABSTRACT

The present invention concerns a bioactive implant material having a cartilage-inducing and/or bone-inducing activity composed of two components A and B, of which A is a bone-inducing and/or cartilage-inducing protein or protein mixture and preferably one or several proteins from the TGF-β superfamily, preferably MP52 or a DNA sequence coding therefor and B is a carrier matrix composed of calcium phosphate ceramics with an interconnecting microporosity which already alone has bone-inducing properties. The invention additionally concerns the production of these compounds and their use for the treatment of diseases which affect cartilage and/or bones as well as to treat damage to cartilage and/or bone tissue.

14 Claims, 1 Drawing Sheet

SEQUENCE LISTING

<160> NUMBER OF SEQ ID NOS: 1

<210> SEQ ID NO 1
<211> LENGTH: 501
<212> TYPE: PRT
<213> ORGANISM: Homo sapiens

<400> SEQUENCE: 1

```
Met Arg Leu Pro Lys Leu Leu Thr Phe Leu Leu Trp Tyr Leu Ala Trp
  1               5                  10                  15

Leu Asp Leu Glu Phe Ile Cys Thr Val Leu Gly Ala Pro Asp Leu Gly
             20                  25                  30

Gln Arg Pro Gln Gly Thr Arg Pro Gly Leu Ala Lys Ala Glu Ala Lys
         35                  40                  45

Glu Arg Pro Pro Leu Ala Arg Asn Val Phe Arg Pro Gly Gly His Ser
 50                  55                  60

Tyr Gly Gly Gly Ala Thr Asn Ala Asn Ala Arg Ala Lys Gly Gly Thr
 65                  70                  75                  80

Gly Gln Thr Gly Gly Leu Thr Gln Pro Lys Lys Asp Glu Pro Lys Lys
                 85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
        195                 200                 205

Gly Gln Asp Asp Arg Gly Pro Val Val Arg Lys Gln Arg Tyr Val Phe
    210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
        275                 280                 285

Ser Gly Trp Glu Val Phe Asp Ile Trp Lys Leu Phe Arg Asn Phe Lys
290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
```

-continued

```
                355                 360                 365
Val Tyr Glu Tyr Leu Phe Ser Gln Arg Arg Lys Arg Arg Ala Pro Leu
        370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
                420                 425                 430

Cys Glu Phe Pro Leu Arg Ser His Leu Glu Pro Thr Asn His Ala Val
            435                 440                 445

Ile Gln Thr Leu Met Asn Ser Met Asp Pro Glu Ser Thr Pro Pro Thr
        450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
                500
```

COMPOUNDS WITH IMPROVED CARTILAGE-INDUCING AND/OR BONE-INDUCING ACTIVITY

Figure 1:
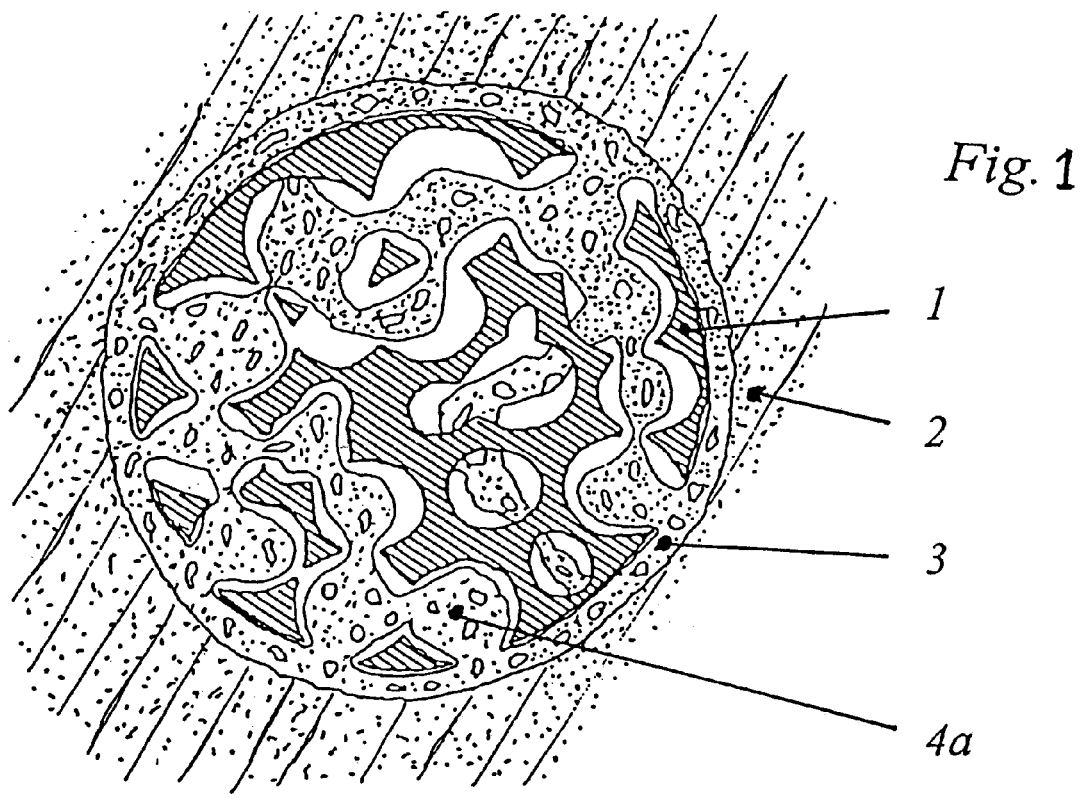

The present invention concerns new improved compounds with cartilage-inducing and/or bone-inducing activity composed of one or several members of the TGF-β family, preferably MP52, or a DNA sequence coding therefor and a special carrier matrix composed of crystallographically phase-pure tricalcium phosphate. The invention additionally concerns the production of these compounds and their use for the treatment of diseases which affect cartilage and/or bones and to treat damage to cartilage and/or bone tissue.

Many growth factors from the TGF-β superfamily are relevant for a wide range of medical treatment methods and applications which in particular concern wound healing and tissue reconstruction. For a review of members of the TGF-β superfamily cf. e.g.: Roberts, A. B. & Sporn, M. B. Handbook of Experimental Pharmacology 95 (1990) 419-472; Kingsley, D. M., Genes & Development 8 (1994) 133-146 and the literature cited therein. The members include the TGF-β proteins such as TGF-β1, TGF-β2, TGF-β3, TGF-β4 and TGF-β5, cf. e.g.: U.S. Pat. No. 5,284,763; EP 0376785; U.S. Pat. No. 4,886,747; Madisen, L. et al., DNA 7 (1988) 1-8; Derynck, R. et al., EMBO J. 7 (1988) 3737-3743; Jakowlew, S. B. et al., Mol. Endo. 2 (1988) 1186-1195; Kondaiah, P. et al., J. Biol. Chem. 265 (1990) 1089-1093. The activins/inhibins which have the previously known activin chains βA, βB, βC and βD form a further subfamily cf. e.g. Mason, A. J. et al., Biochem. Biophys. Res. Commun. 135 (1986) 957-964; Hötten, G. et al., Biochem. Biophys. Res. Commun. 206 (1995) 608-613; Oda, S. et al., Biochem. Biophys. Res. Comm. 210 (1995) 581-588. GDF-12 can also be classed with this subfamily due to its amino acid homology (cf. WO 96/02559). It is known that βA and βB can also form a heterodimer βAβB in addition to the homodimer. Combination with an α subunit forms the inhibins which essentially have the opposite activities compared to activins, cf: Vale, W. et al., Handbook of Experimental Pharmacology 95 (1990) 211-248; Vale, W. et al., The Physiology of Reproduction, Raven Press, New York (1994) 1861-1878. The members of the BMP (bone morphogenetic protein) family form a further subfamily which include the proteins BMP-2 (BMP-2a), BMP-3, BMP-3b, BMP-4 (BMP-2b), BMP-5, BMP-6, BMP-7 (OP-1), BMP-8 (OP-2), BMP-9, BMP-10, BMP-11, BMP-12 and BMP-13 cf. e.g.: Wozney, J. M. et al. Science 242 (1988) 1528-1534; Celeste, A. J. et al., Proc. Natl. Acad. Sci. USA 87 (1990) 9843-9847; Özkaynak, E. et al., J. Biol. Chem. 267 (1992) 25220-25227; Takao et al. Biochem. Biophys. Res. Com. 219 (1996) 656-662; WO 93/00432; WO 94/26893; WO 94/26892, WO 95/16035. A further subgroup is the GDF (growth differentiation factor) family which include GDF-1, GDF-3, GDF-9, GDF-10, GDF-11 as well as GDF-5, GDF-6 and GDF-7 which are particularly interesting for cartilage-induction and/or bone-induction c.f. McPherron, A. C. & Lee, S.-J., J. Biol. Chem. 268 (1993) 3444-3449; Storm, E. E. et al., Nature 368 (1994) 639-643; Lee, S.-J.; Proc. Natl. Acad. Sci. USA 88 (1991) 4250-4254; Cunningham et al. Growth Factors 12 (1995), 99-109; Hötten, G. et al., Growth Factors 13 (1996) 65-74; Chang, S. C. et al., J. Biol. Chem. 269 (1994) 28227-28234. There are some overlaps between the subgroups of the GDF and BMP family due to amino acid homologies. It was also possible to detect a cartilage-inducing potential and bone-inducing potential for the TGF-β superfamily members dpp and 60A from *Drosophila* cf.: Sampath, T. K. et al., Proc. Natl. Acad. Sci. USA 90 (1993) 6004-6008. The proteins dorsalin and the bone formation-inducing protein are also of interest cf.: Basler, K. et al., Cell 73 (1993) 687-702; WO 94/01557. Heterodimers of various members have also been described cf.: Aono, A. et al., Biochem. Biophys. Res. Commun. 210 (1995) 670-677; WO 93/09229; EP 0 626 451. It is known that many members especially from the subfamilies of the TGF-β, BMP and GDF families have a cartilage-inducing and/or bone-inducing potential and members of the activin family can also influence bone formation at least in combination with other TGF-β superfamily members cf. for example Hock, J. M. et al., Endocrinol. 126 (1990) 421-426; Wang et al., Proc. Natl. Acad. Sci. USA 87 (1990) 2220-2224; Wozney et al., Mol. Reprod. Dev. 32 (1992) 160-167; Sampath et al., J. Biol. Chem. 267 (1992) 20352-20362; Ogawa, Y. et al., J. Biol. Chem. 267 (1992) 14233-14237; WO 88/00205; U.S. Pat. No. 5,013,649; WO 89/10409; WO 90/11366; WO 91/05802; WO 92/15323; WO 91/18098; WO 93/00432; WO 93/09229; WO 94/01557; WO 94/26893; WO 94/26892; WO 94/15949; WO 95/01801; WO 95/01802 and EP 0 626 451. Since some of the individual proteins act at different sites during the course of cartilage and bone induction, it can be assumed that a combination of various such proteins would be advantageous for the efficiency of cartilage and bone induction. Such protein mixtures are also encompassed by this invention.

The DNA and protein sequences of proteins of the TGF-β family i.e. MP52 and MP121 are described in WO 93/16099, WO 95/104819 and WO 96/01316. MP121 is the activin βC which has already been mentioned above. MP52 (sometimes also named GDF5 in publications) for which a cartilage-inducing and bone-inducing potential has already been proven is of particular interest (WO 95/04819 and Hötten et al. Growth Factors 13 (1996) 65-74).

The members of the TGF-β superfamily which have a cartilage-inducing and/or bone-inducing potential are characterized in the mature part by high amino acid homologies and have the seven conserved cysteines which are typical for members of the TGF-β superfamily. The active form of members of this superfamily is usually always a homodimeric and/or heterodimeric protein. The cartilage-inducing and/or bone-inducing potential of these proteins is usually tested on inert carrier matrices which themselves have no cartilage-inducing and/or bone-inducing effect at all.

Already in the sixties intensive research work began on the applications of calcium phosphate ceramics as an implantable bone substitute (Bhaskar et al., Oral Surg. 32 (1971) 47) which was based on the chemical similarity of this group of compounds to the mineral component of bone. One of the first systematic investigations on the connections between the chemical and material parameters and the biological properties was carried out at the beginning of the seventies at the Battelle Institute (Heide, Köster et al., Z. Orthop. 118 (1979) 398 and Biotechn. Umschau 2 (1978) 226). In these investigations calcium phosphates with various $CaO/P_2O_5$ ratios were produced by sintering processes as granular and pelleted ceramic implant materials and tested in animal experiments. The major results of these studies can be summarized as follows:

(a) Calcium phosphate ceramics of particular compositions are characterized by an excellent bone tissue tolerance.

(b) The optimum tissue tolerance is mainly achieved with ceramics with a $CaO/P_2O_5$ ratio of 3/1 i.e. with tricalcium phosphate TCP, Ca$_3$(PO$_4$)$_2$ (or written 3CaO.P$_2$O$_5$ as a ceramic formula) and hydroxylapatite (HA) itself i.e. [Ca$_5$(PO$_4$)$_3$OH] which can also be prepared synthetically. This result is logical since it is also known that the composition of the mineral bone component with its most important mineral component hydroxylapatite approximately corresponds to this ratio. Although TCP and HA have a similar chemical composition there are considerable differences in their solubility properties and other physical properties such as density and strength. The potential areas of application also of course depend on this.

(c) The two optimal biocompatible modifications of tricalcium phosphate TCP (i.e. the metastable high temperature modification α-TCP and especially the stable low temperature modification β-TCP) and hydroxylapatite HA are more or less biodegradable i.e. in biological storage they are degraded or absorbed more or less rapidly. α-TCP and β-TCP have a pronounced biodegradability according to Ramselaar et al., J. Materials Sci. 2 (1991) 63. The resorption of HA is very much less in a biological environment. TCP in a bone store tends to be degraded chemically according to experiments with radioactively labelled implant materials by Schuster, Heide et al., (unpublished report of the Battelle Institute Frankfurt) i.e. the dissolution and metabolism of the dissolved products occurs without involvement of bone-degrading cells whereas the very much slower resorption of hydroxylapatite is based more on a specific action of bone-degrading cells (osteoclasts).

(d) The biocompatible calcium phosphate ceramics based on TCP and HA are integrated in the bone store largely without encapsulation by connective tissue as was impressively demonstrated in animal experiments in the seventies by the said Battelle working group among others. At that time the term "bioactivity" was introduced for this outstanding property.

During further development of the promising calcium phosphate ceramics it turned out that detailed knowledge of the complex crystal-chemical relationships of the system CaO—P$_2$O$_5$ (+H$_2$O) is an absolute prerequisite for a systematic optimization. Unfortunately in the past and still today many users ignore these requirements especially when materials based on the poorly biodegradable HA are used for typical temporary applications such as e.g. the sanitation of periodontal pockets. Important papers on this subject have been published by De Groot et al., Biomaterials 1 (1980) 47, and Bauer and Hohenberger, "Berichte der DKG" 66 (1989) 23.

Numerous implant materials that are nowadays still commonly available on the market which are composed of undefined mixtures of TCP and HA and other calcium phosphate phases such as dicalcium or tetracalcium phosphates and calcium phosphate glasses have adverse biomedical properties such as provocation of connective tissue infiltration and activation of macrophages which may be accompanied by inflammatory reactions. The connective tissue encapsulation of materials with such a defective composition is then a manifestation of the rejection of the implant (Bauer and Hohenberger, "Berichte der DKG" 66 (1989) 23). The stoichiometric composition alone is not a criterion for the existence of unphysiological foreign phases. These results lead to the requirement for a crystallographic phase purity of the implant materials that are used.

The two main types of calcium phosphate, tricalcium phosphate (TCP) and hydroxylapatite (HA) have different areas of application corresponding to the differences in their resorption: TCP is particularly advantageous as a temporary bone substitute where in the course of time the biomaterial is resorbed concurrently with bone regeneration (filling of cysts in the jaw area, filling in of bone defects caused by disease or operations or degenerative bone defects etc.). In contrast HA is preferably indicated for long-term bone replacement such as e.g. in connection with the coating of joint endoprostheses where one wants to avoid direct contact of the stressed bone store with metal or other inert materials.

The object of the present invention is to provide new compounds which have particularly high cartilage-inducing and/or bone-inducing activities in mammals and especially in primates such as humans but do not have the disadvantages of the previously used materials or only to the smallest possible extent. Such compounds should greatly accelerate the healing process of diseases which affect cartilage and/or bones and which are in particular associated with a loss of bone substance and/or damage to cartilage and/or bone tissue.

This object is achieved according to the invention by a bioactive implant material for bone replacement with cartilage-forming and/or bone-forming activity composed of two components A and B which comprises a cartilage-inducing and/or bone-inducing protein or protein mixture or DNA coding for such a protein or protein mixture as component A, and a matrix material composed of calcium phosphate which has no intrinsic osteogenic activity as component B, and A is applied to B. Preferred embodiments of the invention are described in the subclaims. In particular a material is provided which is composed of the two components A and B in which A denotes a protein or protein mixture composed of one or several homodimeric or heterodimeric proteins from the TGF-β superfamily with cartilage-inducing and/or bone-inducing activity and B denotes an oesteoinductive carrier matrix preferably composed of a biodegradable bone ceramic particularly preferably of α- or β-tricalcium phosphate ceramics. A is associated with B without being covalently bound and can for example be slowly released from B during the bone formation process to the same extent that B is subject to chemical degradation in the bone store. Hence A is subject to a so-called controlled release.

Alternatively A can also denote a DNA coding for the said proteins or protein mixtures. The DNA can optionally be protected from degeneration by methods known to a person skilled in the art. After release into the surrounding tissue, such a DNA can be taken up by the cells that are present there or by cells that migrate into the carrier matrix and be expressed so that the expressed proteins or protein mixtures act in turn as the active substance.

Hence the DNA is preferably associated with sequences which cause or promote expression. Expression can be promoted especially by specific recombination into the cell genome and namely at a site which leads to the generation of protein under the control of cellular sequences.

On the other hand DNA can also be used on a suitable expression vector.

The term "protein of the TGF-β superfamily with a cartilage-inducing and/or bone-inducing activity" denotes a protein which in its mature part contains the characteristic 7 conserved cysteines. This includes members of the TGF-β, activin, BMP and GDF family and in particular MP52 and fragments thereof with basically the same activity. The corresponding nucleotide and protein sequences are given in the aforementioned citations to the disclosure of which reference is herewith made. These preferably include homodimers of the said proteins and also heterodimers of various family members. Proteins are preferably included which have the same receptor mechanism and/or the same signal transmission as the members of the BMP and/or GDF family, in particular MP52. It also includes a combination of various proteins from the TGF-β superfamily with cartilage-inducing and/or bone-inducing activity. The cartilage-inducing and/or bone-inducing potential can be tested in known experiments such as e.g. in vivo by induction of cartilage and/or bones after implantation of the protein with a suitable carrier matrix into rat musculature; cf. e.g. Sampath, T. K. et al., J. Biol. Chem. 267 (1992) 20352-20362 and/or in vitro by induction of alkaline phosphase activity in ROB-C26 cells; cf. Yamaguchi, A. et al., J. Cell Biol. 113 (1991) 681-687 and/or W-20-17 cells; cf.: Thies, R. S. et al. Endocrinol. 130 (1992) 1318-1324 and/or stimulation of the expression of proteins of the extracellular matrix, cf.: Hock, J. M. et al. Endocrinol. 126 (1990) 421-426 and/or in experiments as described by Chen, P. et al., Exp. Cell Res. 195 (1991) 509-515 and/or Vukicevic, S., et al. Proc. Natl. Acad. Sci. USA 86 (1989) 8793-8797. The protein can be present as a mature protein and also as a precursor protein or a protein in which the propeptide part has been processed in different ways and/or a protein with additional or modified N-terminal and/or C-terminal amino acid sequences which essentially do not influence the biological activity.

On the other hand fusion proteins are also possible which, in addition to the part coding for the mature protein or fragments thereof, additionally still contain functional signal or/and propeptide parts of other proteins in particular of the TGF-β superfamily and especially also of activin, BMP and GDF proteins. The corresponding nucleotide and protein sequences are also found in the above-mentioned citations to the disclosure of which reference is herewith made. It is important that the correct reading frame for the mature protein is retained. Thus for example the exchange of propeptide parts by corresponding parts of other proteins is described in Mol. Endocrinol. 5 (1991), 149-155 and Proc. Natl. Acad. Sci. USA 90 (1993), 2905-2909.

The protein in the compound according to the invention or the protein coded thereby can contain substituted or inserted amino acids or contain deletions, also provided that the activity is not significantly influenced and can be isolated from various species such as e.g. humans, mouse, rat, cow or pig. Furthermore the protein can be modified by methods known in the prior art such as glycosylations, phosphatizations, sulfations and esterification with fats also provided that this does not result in a significant change in the activity.

In a preferred embodiment of the present invention A is a protein from the GDF or BMP family or a fragment thereof.

In a particularly preferred embodiment of the present invention the component A is characterized by a protein which (a) contains the mature part and optionally additional functional parts of the protein sequence shown in SEQ ID NO. 1,
(b) contains parts of the mature part of (a) which have essentially the same activity, in particular mature proteins with a modified N-terminus,
(c) contains parts corresponding to (a) or (b) which differ from SEQ ID NO:1 due to the origin of the protein from other vertebrates but have essentially the same activity,
(d) in addition to containing parts of the mature protein according to (a), (b) or (c), also contains parts of another protein from the TGF-β superfamily in the form of a fusion protein,
(e) in addition to containing monomeric mature proteins according to (a) to (d), also contains a monomer of another protein from the TGF-β superfamily with formation of heterodimers,
(f) in addition to containing dimeric mature proteins according to (a) to (e), also contains at least one dimer of another protein from the TGF-β superfamily.

This embodiment in particular comprises the mature protein MP52 or functional parts or fragments thereof in which the active form is preferably present as a dimer. Functional regions or sections or fragments are particularly preferred which contain at least the region of the seven conserved cysteines.

A "biocompatible" and "bioactive" carrier matrix denotes in the osteological sense a calcium phosphate ceramic which, on the one hand, can be integrated into bones without damaging tissue reactions such as connective tissue encapsulations, inflammations and tissue degenerations and, on the other hand, stimulates a direct growth of bones onto or into the surface structure of the implant. However, "bioactivity" of a carrier matrix is not present until a histologically and clinically detectable stimulation of bone growth occurs. There is clinical experience with the highly porous bioactive carrier matrix (such as e.g. Cerasorb®) according to the invention which is based on tricalcium phosphate, in particular on β-TCP and also α-TCP. The phase-pure and open microporous β-TCP has an outstanding position with regard to bioactivity or osteoinductivity and alone produces an ion environment as a result of the predictable chemical dissolution in the bone store which contributes to the stimulation of osteoblast activity and in situ serves as a substrate for osteoblast activity. If the chemical dissolution or resorption of the carrier matrix occurs simultaneously with the primary phase of bone formation (woven bone phase) there is an excellent chance of regaining the strength and structure of the surrounding bone store. A prerequisite for this is the absence of unstoichiometric secondary phases which often react unphysiologically. This can be demonstrated for phase-pure β-TCP and it therefore already alone has an osteoinductive action. Crystallographically phase-pure α- or β-tricalcium phosphate ceramics with an interconnecting microporosity in the range of 20-60% of their volume are particularly preferred. In a particularly preferred embodiment the primary particle size of the crystallographically phase-pure α- or β-tricalcium phosphate ceramics is in the range of 10-40 μm. In a further preferred embodiment of the invention this implant material is present in the form of an injectable suspension. This for example enables the material to be applied with a minimum of invasiveness. Hence a suspension of this matrix in suitable liquids for medical applications such as water, serum, plasma and blood does not cause any infiltration of giant cells or connective tissue into the implant.

Hence an important subject matter of the invention is an implant material composed of two components A and B in which the osteopoetic effect of component A is synergistically amplified by an osteoinductive effect of component B. Hence the compound is based on an advantageous combination of mechanisms of action of two components i.e. a cartilage-inducing and/or bone-inducing protein or protein mixture and an osteoinductive carrier matrix. Such an implant material according to the invention avoids counter-productive effects with regard to the osteopoetic effect of the proteins A which some biocompatible but not bioactive implant materials exhibit. Thus carrier materials such as HA are often unsuitable for an application in protein-stimulating oestosynthesis due to their slow biodegradability. Rapidly biodegradable carrier ceramics such as phosphate glasses and metastable phases or phase mixtures of CaP and also of chemically modified matrices which are for example obtained from corals have already alone a counter-productive effect on protein-stimulating osteosynthesis due to the activation of macrophages or/and osteoclasts. Furthermore it has turned out that coating the matrix surface of suitable carrier materials with physiologically inert protein fillers such as collagen has an inhibitory effect on resorption and thus on bioactivity. Surprisingly mixtures of carrier materials based on microporous phase-pure TCP, preferably β-TCP, with homogenates of red bone marrow or blood have been shown to promote osteosynthesis despite the considerable coverage of the matrix surface with proteins. Hence the implant materials according to the invention represent an optimization of these results. The minimal matrix coverage with the protein or DNA component A ensures the maintenance of the bioactive, i.e. intrinsic, osteoinductive properties of the carrier matrix B from which component A is inevitably released through its interconnecting micropore structure and is thus biologically active to an extent corresponding to the chemical degradation of the matrix at the site of implantation. If it were not combined with a suitable matrix, the osteopoetic protein A alone would rapidly lose its biological activity at the site of implantation due to metabolism, transport by body fluids or phagocytosis. The phase purity of the carrier matrix with a defined micropore structure ensures a predictable resorption and thus also a controlled release of the protein component A or of a DNA coding therefor. Such an interaction between matrix B and protein A undoubtedly represents a synergistic amplification of the effects of the two components A and B.

A further subject matter of the present invention is a process for the production of the implant materials according to the invention in which a solution of the protein A or DNA in a physiologically acceptable, water-miscible solvent or in appropriate solvent mixtures is applied to the microporous structure of the biocompatible matrix B in such a way that the component A is distributed homogeneously in and/or on the microporous structure of the matrix.

Information on the production of proteins of the TGF-β superfamily, their expression in suitable host cells and purification may be found in numerous already cited publications and patent documents. In particular reference is made to WO 95/04819 and DE 19525416.3 as well as to Hötten et al. (Growth Factors 13 (1996) 65-74) for the preparation of MP52/GDF-5 or active fragments thereof.

If the proteins are produced in bacteria where the proteins are present in the form of inclusion bodies as is the case for MPS2, they are renatured by known methods in order to obtain the protein, for example MP52, in an active form. MP52-like proteins expressed in *E. coli* can be refolded into an active protein cf.: Krieglstein, K. et al., J. Neuroscience Res. 42 (1995) 724-732. Exact procedures are also described in the Japanese Patent Application Hei 7('95)-93664 as well as in DE 19525416.3. Other investigations by us as well as by Ruppert, R. et al. (Eur. J. Biochem. 237, 295-302 (1996)) have shown that for example BMP-2 can also be expressed in *E. coli* and refolded to form the dimer.

The DNA is prepared by methods known to a person skilled in the art as described for example in Current Protocols in Molecular Biology (Ausubel et al., Greene Publishing Associates and Wiley-Interscience, Wiley & Sons, 1987-1996) or in Molecular Cloning (Sambrook et al., second edition, Cold Spring Harbor Laboratory Press 1989).

The following procedure according to DE 38 10 803 C2 can be used to prepare the carrier matrix B: homogeneous stoichiometric mixtures of $CaCO_3$ and $CaHPO_4$ are subjected in various steps to sintering temperatures up to 1350° C. in compacted moulded bodies according to the constitution diagram (phase diagram) of the system CaO and $P_2O_5$ (Trömel, Stahl und Eisen 63 (1943) 21; Welch, J. Chem. Soc. (1961) 4442) in which water and $CO_2$ are removed from the sintering system. Between the sintering processes the intermediate stages of the sintering synthesis are comminuted, micronized, recompacted for the production of moulded articles or pelletized for granulate production. The sintering processes are carried out with respect to time and temperature such that coexisting neighbouring phases of TCP according to the phase diagram are avoided i.e. in particular tetra calcium phosphate on the one hand and dicalcium phosphate on the other hand. Metastable phases of the thermodynamically stable $β-Ca_3(PO_4)_2$ or β-TCP can either be specifically avoided by regulating the sintering process according to the intended application or can be intentionally made to coexist or can even be prepared alone as the dominant product.

A homogeneous incorporation and distribution of the component A in the pore structure of the carrier matrix B requires several types of process which enable such a distribution without the component itself being changed by the processes.

Thus it is obvious that a combination of A and B cannot be used simultaneously in the ceramic sintering process due to the high process temperatures.

In contrast it is possible to penetrate the microporous ceramic structure of the moulded parts and granulate particles with solutions of the proteins A or the DNA coding therefor according to the invention in suitable solvents in which the capillary forces of the open ceramic structure become effective. When selecting solvents, of course only those come into consideration which do not alter the characteristics of the components A and B of the biomaterial. Thus for example acidic solvents are unsuitable which although being excellent solvents for osteopoetic proteins, attack and chemically modify the calcium phosphates. On the other hand water is neutral towards ceramics but is often only able to incompletely dissolve the protein components A. A penetration by means of suspensions would not allow a homogeneous distribution in the carrier matrix due to the microporous structure.

A process for penetrating the carrier matrix by means of the solvent phase which could obviously be driven out by evaporation, also does not lead to a completely homogeneous distribution of A in B since when the solvent evaporates on the surface of the porous ceramics there is a mass transport of the dissolved phase from the inside to the outside resulting in a concentration on the surface.

A solution for this complex problem of homogeneously dosing the carrier matrix with component A can be accomplished according to the invention by the following types of process:

Removing the solvent after cooling a gently heated solution saturated with the proteins A. As a result the limit of solubility of the proteins in the solvent is exceeded and the proteins are deposited in the carrier structure. This reduces the amount of protein in the remaining solution and correspondingly reduces the described concentration effect. There is a natural limit to this method due to the small temperature margin, but it is especially appropriate when a quantity gradient of the protein in the ceramic structure is desirable with regard to a certain starter effect on osteopoesis.

Removing a protein-containing or DNA-containing liquid mixture composed of organic solvent and/or water by sublimation according to critical point drying. The direct transition of the solidified solvent mixture into the gaseous state prevents transport of the protein or the DNA via the liquid phase and results in a uniform distribution of the precipitated protein or the DNA in the ceramic structure.

Homogeneous precipitation of protein in the ceramic carrier structure from a protein-containing organic solution by adding for example water which leads to a rapid precipitation of the protein and thus to an in situ deposition in the ceramic structure. This method can be used in various ways and works with substance pairs in which the protein is soluble in the organic solvent, the pure solvent is miscible with water but not the protein-containing solution. Acetonitrile/water, propanediol-1,2/water or propanol/water can, among others, for example be used for this.

Homogeneous precipitation of DNA in a ceramic carrier structure from a DNA-containing salt solution (for example 0.1 M NaCl or 0.25 M NaAc) by adding an alcoholic solution such as absolute ethanol which leads to a rapid precipitation of the DNA in the ceramic structure. The doped carrier matrix can if necessary be washed with 70% ethanol.

The efficacy of the implant materials according to the invention can be tested in conventional test systems such as e.g. the already mentioned rat, dog, rabbit or also primate animal models.

Further subject matters of the present invention are therefore a pharmaceutical composition containing an implant material optionally together with pharmaceutically as well as physiologically acceptable auxiliary substances, diluents and/or fillers and the use of the compounds according to the invention at a pharmaceutically effective concentration optionally together with pharmaceutically as well as physiologically acceptable auxiliary substances, diluents and/or fillers for the local treatment of cartilage and/or bone diseases and/or of damage to cartilage and/or bone tissue caused by injury, operation, degeneration or strain in vertebrates and in particular in mammals such as humans.

The compounds according to the invention can be used to specifically treat diseases which are associated with bone loss caused for example by age, metabolic diseases or inflammatory processes.

Damage to cartilage or bone tissue can occur after injury such as sport injuries, accidents, straining the apparatus of locomotion or can occur as a result of operations for example due to drill holes in the bones after removing screws for artificial fastening apparatuses or after resections of tumour tissue. The specific local treatment of bone fractures is particularly preferred. It is also possible to elongate limbs. Applications in the dental or jaw region are of particular interest such as the treatment of perioaontosis, sinus lift or cyst filling in the jaw area. There are also applications in cosmetic surgery in particular plastic surgery in the facial region. The compounds according to the invention also enable two movable bone parts to be immobilized such as e.g. the connection of two vertebrae by means of a newly formed bone bridge which can for example be advantageous for intervertebral disk problems. The said methods of treatment also include veterinary medicine.

The dose is in the range of 10 µg to 100 mg depending on the type of protein component and on the type of application, the disease and the state of the patient. The amount of carrier matrix depends on the size of the bone or cartilage defect which is to be treated.

If large pressed carrier matrices are used they have to be mechanically fixed by for example steel rods and screws.

The synergistic effect which is the basis of this invention achieved by combining mechanisms of action of two components in a compound i.e. cartilage-inducing and/or bone-inducing protein and osteoinductive carrier matrix enables very good results to be achieved in treatments.

An advantage of the implant materials according to the invention is that it is possible to substantially improve and accelerate healing processes that require cartilage-inducing and/or bone-inducing reactions. This advantageously results in a considerable reduction of the period of suffering for the patients, shorter periods out of work and a reduction of the costs for hospital stays. A further economic aspect is the effective treatment of the wide-spread disease periodontosis which is accompanied by a premature loss of teeth. Thus economically tooth preservation made possible by periodontosis treatment contrasts with expensive premature dentures.

A short description of the figures follows:

SEQ ID NO. 1 shows the complete amino acid sequence of the precursor protein of the human TGF-β protein MP52. The start of the mature protein is preferably in the region of amino acids 361-400, particularly preferably at amino acid 381 or 382. The mature part of the protein contains the seven conserved cysteines at positions 400, 429, 433, 465, 466, 498 and 500.

Figure 2:
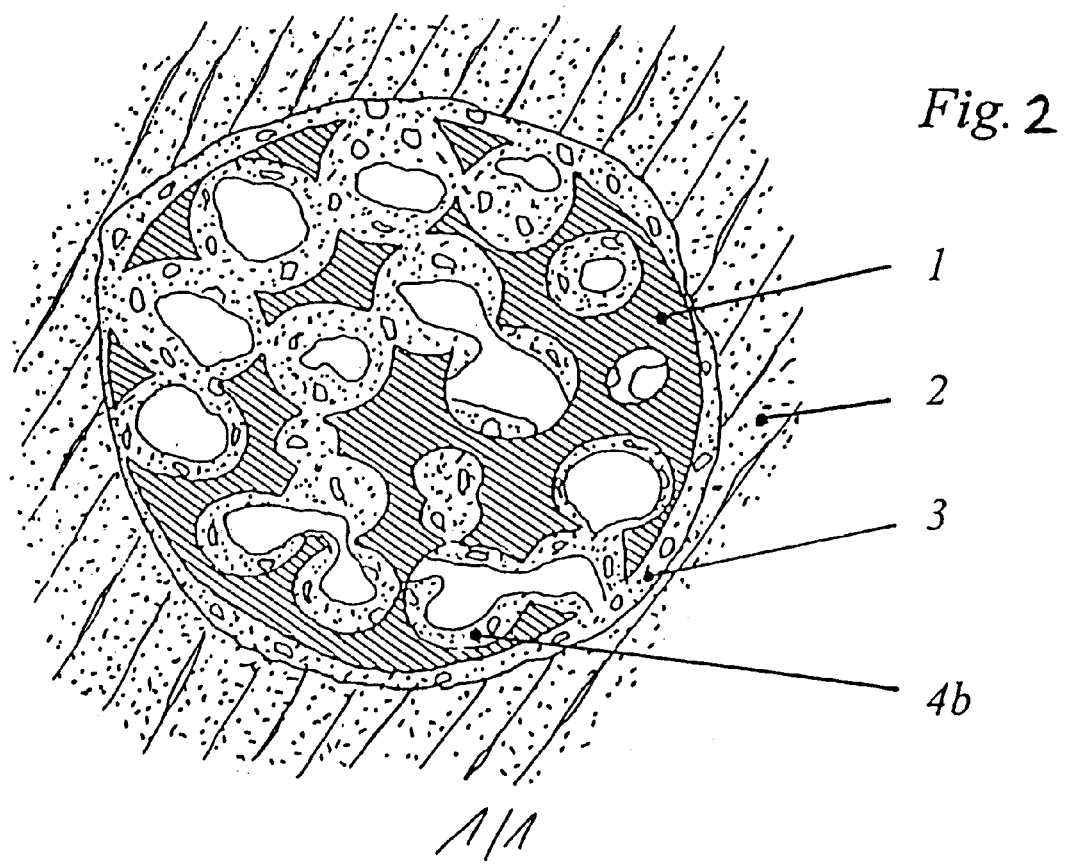

FIGS. 1 and 2 show the osteoinductive effect of the carrier matrix according to the invention compared to a biocompatible but not bioactive matrix.

FIGS. 1 and 2 show the osteoinductive activity of the carrier matrix according to the invention as compared with the biocompatible, albeit not bioactive matrix. FIG. 1 schematically shows the bone formation in the pores of a bioinert matrix e.g. $Al_2O_3$ (1 in FIG. 1). FIG. 2 in comparison shows the osteoinductive effect of the calcium phosphate matrix according to the invention (1 in FIG. 2) in an otherwise identical implant situation.

In both cases cylindrical implants (1) (outer diameter: 6 mm) having an open macroporosity throughout (pore diameter ca. 0.5 to 0.7 mm Ø) were implanted into compact bones (tibia of a dog). The compact storage bone (2) having a clearly visible lamellar structure forms new bone around the implant after a short implantation period which attempts to bridge the intermediate space between the drilled hole in the bone and the outer edge of the implant (3). In addition new bone also forms in the pores of the implant (4a in FIGS. 1 and 4b in FIG. 2).

The significant difference between the two implant materials is that the bone in the osteoinductive implant material (4b in FIG. 2) is formed immediately and spontaneously on the inner surfaces of the pores and the carrier matrix is used as a site of nucleation and from there fills the entire implant region. In contrast the bone grows very slowly in the non-bioactive material (FIG. 1) through the middle of the pores and permanently avoids direct contact with the implant material. These differences result in a very intensive and rapid composite formation in the case of the osteoinductive material (FIG. 2) and in a delayed incomplete formation in the case of the bioinert material which is accompanied by osteoclast activity (FIG. 1).

The invention claimed is:

1. An implant material suitable for cartilage, bone, or cartilage and bone growth comprising a matrix material which is composed of a crystallographically phase-pure calcium phosphate and applied in and/or on said matrix a cartilage inducing, bone inducing, or cartilage and bone inducing MP52 protein, wherein the MP52 protein is selected from the group consisting of
   (a) a protein comprising amino acid 1 to 501, 28 to 501, 361-400 to 501, 381 to 501, or 382 to 501 of SEQ ID NO. 1, and
   (b) a protein according to (a) which is a homodimer.

2. The implant material of claim 1, wherein the matrix material is composed of a tricalcium phosphate ceramic comprising crystallographically phase-pure α or β-tricalcium phosphate ceramic with an interconnecting microporosity of 20-60% of its volume.

3. The implant material of claim 2, wherein the α- or β-tricalcium phosphate ceramic has a primary particle size of 10-40 μm and causes no giant cell or connective tissue infiltration into the implant material.

4. The implant material of claim 2, wherein it is present in the form of an injectable suspension.

5. The implant material of claim 2, wherein the matrix degrades over time to release the MP52 protein in a controlled retarded manner.

6. A process for the production of an implant material according to claim 1, the process comprising applying the MP52 protein in and/or on the matrix as a solution in a solvent such that a homogeneous distribution of the MP52 protein in and/or on the calcium phosphate matrix is achieved.

7. The process of claim 6, wherein the solvent is removed by sublimation.

8. The process of claim 6, wherein the MP52 protein is concentrated by in situ precipitation from the solvent in the matrix by admixing a precipitating solvent.

9. A pharmaceutical composition comprising an implant material according to claim 1 and a liquid suitable for preparing a pharmaceutical suspension.

10. A method of treating a disease or condition where the growth of bone and/or cartilage is desirable in a patient in need thereof, the method comprising implanting an implant material according to claim 1, to the site where the bone and/or cartilage growth is desired in the patient.

11. A method of inducing at least one of bone or cartilage growth in a patient in need thereof, the method comprising implanting an implant material according to claim 1, to the site where the bone and/or cartilage growth is desired in the patient.

12. A method for inducing bone growth for the treatment of a bone defect or bone fracture where the growth of bone is desirable, for application in the jaw region or dental region or for immobilizing movable bone parts in a patient, comprising implanting an implant material according to claim 1, to the bone defect or bone fracture site in into the patient.

13. The method according to claim 12, for the treatment of periodontosis.

14. An implant material suitable for cartilage, bone, or cartilage and bone growth comprising a matrix material which is composed of a crystallographically phase-pure calcium phosphate and applied in and/or on said matrix a cartilage inducing, bone inducing, or cartilage and bone inducing MP52 protein, wherein the MP52 protein is selected from the group consisting of
   (a) a protein comprising amino acid 1 to 501 or 382 to 501 of SEQ ID NO. 1, and
   (b) a protein according to (a) which is a homodimer.

* * * * *